(12) United States Patent
de Smidt et al.

(10) Patent No.: US 8,012,494 B2
(45) Date of Patent: Sep. 6, 2011

(54) PHARMACEUTICAL COMPOSITIONS CONTAINING LIPASE INHIBITORS

(75) Inventors: Passchier Christiaan de Smidt, Pamplona (ES); Paul Hadvary, Biel-Benken (CH); Hans Lengsfeld, Basel (CH); Thomas Rades, Dunedin (NZ); Hans Steffen, Liestal (CH); Joseph Tardio, St. Louis (FR)

(73) Assignee: Hoffmann-La Roche Inc., Nutley, NJ (US)

( * ) Notice: Subject to any disclaimer, the term of this patent is extended or adjusted under 35 U.S.C. 154(b) by 1213 days.

(21) Appl. No.: 10/794,123

(22) Filed: Mar. 5, 2004

(65) Prior Publication Data

US 2004/0175420 A1   Sep. 9, 2004

Related U.S. Application Data

(63) Continuation of application No. 10/419,346, filed on Apr. 21, 2003, now abandoned, and a continuation of application No. 09/660,297, filed on Sep. 13, 2000, now abandoned.

(30) Foreign Application Priority Data

Sep. 13, 1999 (EP) .................................. 99118180

(51) Int. Cl.
*A61K 9/00* (2006.01)
*A61K 31/70* (2006.01)
*A61K 31/335* (2006.01)

(52) U.S. Cl. ........... 424/400; 514/23; 514/449; 514/547
(58) Field of Classification Search .................. 424/400; 514/23, 449, 547
See application file for complete search history.

(56) References Cited

U.S. PATENT DOCUMENTS

| 4,598,089 A | 7/1986 | Hadvary et al. |
| 4,950,484 A * | 8/1990 | Olthoff et al. ................. 424/464 |
| 5,643,874 A | 7/1997 | Bremer et al. |
| 5,891,469 A * | 4/1999 | Amselem ....................... 424/451 |
| 6,004,996 A * | 12/1999 | Shah et al. ..................... 514/449 |
| 6,147,108 A | 11/2000 | Hauptman |
| 6,368,622 B2 * | 4/2002 | Chen et al. .................... 424/464 |

FOREIGN PATENT DOCUMENTS

| EP | 0 638 317 B1 | 2/1995 |
| WO | WO 97/31003 A1 | 8/1997 |
| WO | WO 98/08490 A1 | 3/1998 |
| WO | WO 98/34607 | 8/1998 |
| WO | WO 98/34630 | 8/1998 |
| WO | WO 99/34786 | 7/1999 |
| WO | WO 00/09122 | 2/2000 |
| WO | WO 00/09123 | 2/2000 |

OTHER PUBLICATIONS

Merck Index, 12 Edition (1996), p. 1307.
Merck Index, 13 Edition (1996), p. 1177.
Gennaro, A. Remington Farmacia, 19ed. Ed. Medica Panamericana, Buenos Aires (1995).
Helman, J., Farmacotecnica Teorica y Practica, 3ed. Ed. Continental S.A. Mexico p. 1829, 1830, 2009-2031 (1982).
Lookene A., et al., Eur. J. Biochem 222, pp. 395-403 (1994).
Hirokawa Publishing Co., Manual of Japan Pharmacopeia, 13th revision (1996).
Noburu Hoshi, et al., Handbook for Medicine Additive, pp. 40-41 (1992).

* cited by examiner

*Primary Examiner* — Johann Richter
*Assistant Examiner* — Luke Karpinski
(74) *Attorney, Agent, or Firm* — George W. Johnston; John P. Parise

(57) ABSTRACT

A pharmaceutical composition comprises at least one inhibitor of lipases, preferably an inhibitor of gastrointestinal and pancreatic lipases, such as orlistat, at least one surfactant, and at least one dispersant.

23 Claims, No Drawings

PHARMACEUTICAL COMPOSITIONS CONTAINING LIPASE INHIBITORS

This application is a continuation of U.S. patent application Ser. No. 10/419,346, filed Apr. 21, 2003, currently pending, which is a continuation of U.S. patent application Ser. No. 09/660,297, filed Sep. 13, 2000, which is abandoned.

BACKGROUND OF THE INVENTION

1. Field

The present invention relates to pharmaceutical compositions comprising lipase inhibitors.

2. Description

Examples of lipase inhibitors include lipstatin and orlistat. The latter is also known as tetrahydrolipstatin or THL and is derived from a natural product excreted by *Streptomyces toxytricini*. This class of compounds was found to exhibit in vitro as well as in vivo activity against various lipases, such as lingual lipase, pancreatic lipase, gastric lipase, and carboxylester lipase. Its use for the control or prevention of obesity and hyperlipidemia is described, for instance, in U.S. Pat. No. 4,598,089.

Orlistat is currently administered at doses of 120 mg per meal and dosing is independent of the body mass of the human subject. Orlistat acts locally in the gastrointestinal (GI) tract and prevents lipase from digesting triglycerides and subsequently inhibits the formation of absorbable lipid degradation products. For this reason, systemic availability of the lipase inhibitors is not required and, instead, local residence in the gastrointestinal tract is preferred.

Lipase inhibitor compositions currently administered inhibit around 30% of fat absorption after consumption of a mixed meal; an increase of the lipase inhibitors concentration in the pharmaceutical composition does not increase its clinical efficacy while the intensity of local side effects increases.

Anal leakage of oil (oily spotting) is an adverse effect that is occasionally observed in patients treated with lipase inhibitors. This phenomenon reflects physical separation of some liquid unabsorbed dietary fat from the bulk of solids in the lower large intestine.

There has been a long felt need for lipase inhibitor compositions that improve the clinical efficacy and/or potency of the inhibitor itself, and/or to minimize or suppress the above mentioned disadvantages.

SUMMARY OF THE INVENTION

The subject invention provides a pharmaceutical composition comprising at least one lipase inhibitor, at least one surfactant, and at least one dispersant.

Favorable lipase inhibitors are inhibitors of gastrointestinal and pancreatic lipases, for example orlistat. Such lipase inhibitors are oftentimes present in an amount from 1% to 50% of the total weight of the composition, and more preferably from 5% to 30% of the total weight of the composition.

Typically, dispersants are water-soluble, for example sugars, sugar alcohols, alcohols, effervescents, excipients, capsule disintegrants, tablet disintegrants, and mixtures thereof. Preferred dispersants include glucose, sorbitol, mannitol, maltodextrin, lactose, sucrose, polyethylenglycol, glycerol, triacetin, glycofurol, effervescents, and mixtures thereof, and are more favorably sorbitol, mannitol, maltodextrin, lactose, sucrose, polyethylenglycol, glycerol, triacetin, glycofurol, and mixtures thereof.

Dispersants can also be lipid-soluble compounds that are liquid at body temperature. Preferred lipid-soluble compounds include triglycerides, modified triglycerides, diglycerides, modified digliclycerides, monoglycerides, modified monoglycerides, mixtures of modified or non-modified di/mono/triglycerides, vitamin E, tocopherol acetate, terpenes, squalene, and mixtures thereof, more preferably triglycerides, diglycerides, monoglycerides, mixtures of mono/di/triglycerides, vitamin E, tocopherol acetate, and mixtures thereof. Favored lipid-soluble compounds include medium chain triglycerides or a mixture of medium chain triglycerides.

The dispersant usually is present in an amount of at least 5% of the total weight of the composition, for example between 5% and 70% of the total weight of the composition. It is beneficial to use a lipid-soluble compound present in an amount varying between 20 and 90% of the total weight of the composition.

Preferred surfactants include anionic surfactants, cationic surfactants, non-ionic surfactants, zwitterionic surfactants, and mixtures thereof. Favorable surfactants include vitamin E polyethylene glycol 1000 succinate, polyoxyethylene sorbitan fatty acid esters, polyoxyethylene stearates, polyoxyethylene alkyl ethers, polyoxyethylene castor oils, polyglycolyzed glycerides, transesterified and (poly)ethoxylated oils, sorbitan fatty acid esters, poloxamers, fatty acids salts, bile salts, alkylsulfates, lecithins, mixed micelles of bile salts and lecithins, sugar esters, and mixtures thereof. As especially preferred group of surfactants include vitamin E polyethylene glycol 1000 succinate, polyethoxylated castor oil, and polyethylene glycol 40 stearate. Surfactant is generally present in an amount of at least 0.1% of the total weight of the composition, and more preferably 0.1% to 90% of the total weight of the composition. Two or more surfactants can be combined.

The above-mentioned inventive pharmaceutical compositions may further comprise pharmaceutically acceptable excipients, such as carbohydrates, antioxidants, co-solvents, as well as thickening agents, preservatives, and lubricants.

An advantageous group of the subject inventive pharmaceutical compositions include 1% to 50% lipase inhibitor of the total weight of the composition, 5% to 70% of at least one dispersant of the total weight of the composition, and 0.1% to 90% of at least one surfactant of the total weight of the composition. These compositions may further include one or more pharmaceutically acceptable excipients.

DETAILED DESCRIPTION OF THE PREFERRED EMBODIMENTS

The subject invention will be described in terms of its preferred embodiments. These embodiments are set forth to aid in understanding the invention but are not to be construed as limiting.

The subject neither provides a pharmaceutical composition containing at least one inhibitor of lipases, at least one surfactant and at least one dispersant.

"Dispersants" or "dispersing agents" are materials that facilitate the initial disintegration of the composition and promote further fine distribution in the environment.

A "surfactant" (surface-active agent) is a substance such as a detergent that, when added to a liquid, reduces its surface tension between a lipophilic and a hydrophilic phase. The surface-active molecule must be partly hydrophilic (water-soluble) and partly lipophilic (soluble in lipids, or oils). It concentrates at the interfaces between bodies or droplets of water and those of oil, or lipids, to act as an emulsifying agent, or foaming agent. Preferred surfactants are anionic, cationic, non-ionic and zwitterionic surfactants.

The term "lipase inhibitor" or "inhibitor of lipases" refers to compounds that are capable of inhibiting the action of lipases, for example gastric and pancreatic lipases. For example orlistat and lipstatin as described in U.S. Pat. No. 4,598,089 are potent inhibitor of lipases. Lipstatin is a natural product of microbial origin, and orlistat is the result of a hydrogenation of lipstatin. Other lipase inhibitors include a class of compound commonly referred to as panclicins, analogues of orlistat. The term "lipase inhibitor" refers also to polymer bound lipase inhibitors for example described in International Patent Application WO99/34786 (Geltex Pharmaceuticals Inc.). These polymers are characterised in that they have been substituted with one or more groups that inhibit lipases. The term "lipase inhibitor" also comprises pharmaceutically acceptable salts of these compounds. The term "lipase inhibitor" preferably refers to orlistat.

Orlistat is known to be useful for the control or prevention of obesity and hyperlipidemia. See, U.S. Pat. No. 4,598,089, issued Jul. 1, 1986, which also discloses processes for making orlistat and U.S. Pat. No. 6,004,996, which discloses appropriate pharmaceutical compositions. Further suitable pharmaceutical compositions are described for example in International Patent Applications WO 00/09122 and WO 00/09123.

Orlistat is preferably orally administered from 60 to 720 mg per day in divided doses two to three times per day. Preferred is wherein from 180 to 360 mg, most preferably 360 mg per day of a lipase inhibitor is administered to a subject, preferably in divided doses two or, particularly, three times per day. The subject is preferably an obese or overweight human, i.e. a human with a body mass index of 25 or greater. Generally, it is preferred that the lipase inhibitor be administered within about one or two hours of ingestion of a meal containing fat. Generally, for administering a lipase inhibitor as defined above it is preferred that treatment be administered to a human who has a strong family history of obesity and has obtained a body mass index of 25 or greater.

It has surprisingly been found that administering a lipase inhibitor in a composition containing at least one surfactant and at least one dispersant improves the efficacy and/or potency of the lipase inhibitor itself. Furthermore, the intersubject variability in efficacy and/or potency is reduced, as well as the frequency and intensity of side effects.

The pharmaceutical compositions according to the present invention have been found to exhibit very favorable effects when applied orally during meal intake in humans. Surprisingly, an increased efficacy and/or potency compared to the already known compositions was observed. This was unexpected as the compositions according to the invention form, at least in part, micellar or finely dispersed (micron or submicron range) materials.

Furthermore, the compositions according to the present invention induce less unpleasant side effects in the single meal test than the already known compositions, despite the greater amount of fat that remains unabsorbed. During the single meal studies with human subjects, it was observed that the stools obtained after intake of compositions according to the present invention show less separation of oil from the main stool mass as compared to the conventional compositions. This was unexpected, as equal or higher amounts of fat were present in the collected stools.

According to the present invention, the lipase inhibitor, preferably an inhibitor of gastrointestinal and pancreatic lipases, most preferably orlistat, is present in an amount varying from 1 to 50%, preferably 5 to 30%, of the total weight of the composition.

The presence of at least one surfactant optimizes particle distribution in the stomach. In a preferred embodiment of the present invention, the surfactant is selected from the group consisting of anionic surfactants, cationic surfactants, nonionic surfactants, zwitterionic surfactants and mixtures thereof. More preferred are surfactants chosen among the group consisting of vitamin E polyethylene glycol 1000 succinate (TPGS), polyoxyethylene sorbitan fatty acid esters, polyoxyethylene stearates, polyoxyethylene alkyl ethers, polyglycolyzed glycerides, transesterified and (poly)ethoxylated oils, polyoxyethylene castor oils, sorbitan fatty acid esters, poloxamers, fatty acid salts, bile salts, alkylsulfates, lecithins, mixed micelles of bile salts and lecithins, sugar esters and mixtures thereof.

"Polyoxyethylene sorbitan fatty acid esters" are commercially available and refer to mono-, di- or tri-ester of sorbitan with fatty acids ($C_8$ to $C_{18}$), e.g. POE(20) sorbitan monolaurate (Polysorbate 20), POE(20) sorbitan monopalmitate (Polysorbate 40), POE(20) sorbitan monostearate (Polysorbate 60), POE(20) sorbitan tristearate (Polysorbate 65), POE (6) sorbitan monostearate (PEG-6 Sorbitan Stearate), POE (20) sorbitan monooleate (Polysorbate 80), POE(20) sorbitan monooleate (Polysorbate 80), POE(20) sorbitan trioleate (Polysorbate 85), POE(6) sorbitan monooleate (PEG-6 sorbitan oleate), and POE(20) sorbitan monoisostearate (PEG-20 Sorbitan Isostearate).

The term "polyoxyethylene stearates" refers to polyoxyethylene glycol esters with stearic acid, e.g. PEG 22 stearate, PEG 32 stearate, and PEG 40 stearate. These compounds are known in the art and commercially available.

The term "polyoxyethylene alkyl ethers" refers to ether composed of polyoxyethylene and alkyl groups, e.g. POE(7) C12-14 alkyl ether, POE(9) C12-14 alkyl ether, POE(3)C12-14 alkyl ether, and POE(9)C12-14 alkyl ether.

"Transesterified and (poly)ethoxylated oils" are surfactants that have been chemically modified by a) a saponification reaction and b) a re-esterification with fatty acids and/or polyethylenglycol (PEG).

The term "polyglycolyzed glycerides" refer to glycerides that are partially esterified with fatty acids and polyethylenglycol (PEG). Examples are polyglycolyzed glycerides, 44/14, saturated polyglycolyzed glycerides, 50/13, and saturated polyglycolyzed glycerides, 53.

The term "polyoxyethylene castor oils" refers to castor oil that has been esterified with polyethyleneglycol, e.g. polyoxyl 35 castor oil (Cremophor EL), PEG-30 castor oil, PEG-40 castor oil, PEG-25 hydrogenated castor oil, and PEG-40 hydrogenated castor oil.

The term "fatty acid salts" refers to pharmaceutically acceptable salts of $C_{12}$ to $C_{18}$ fatty acids, preferably natural fatty acids, e.g. Mg-stearate.

The term "alkyl sulfates" refers to $C_{12}$ to $C_{18}$ alkylsulfates, e.g. sodium dodecylsulfate.

The term "sorbitan fatty acid esters" refers to esters of $C_{12}$ to $C_{18}$ fatty acids, preferably natural fatty acids, like sorbitan laurate, sorbitan oleate, sorbitan palmitate, sorbitan stearate, sorbitan tristearate, sorbitan trioleate, etc.

The term "lecithin" refers to natural or synthetic lecithin. A lecithin has the following structure:

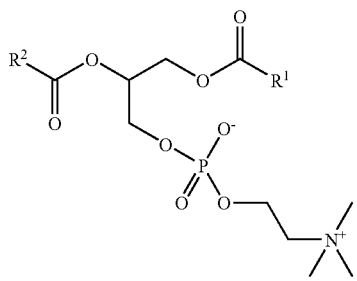

wherein $R^1$ and $R^2$ are fatty acids as defined herein (see definition for fatty acid salts). Lecthins may be chosen from the group consisting of natural lecithin, synthetic lecithin, soya lecithin, egg lecithin, synthetic dipalmitinlecithin, partially or fully hydrogenated lecithin and mixtures thereof.

The term "bile salts" refers to pharmaceutically acceptable salts, e.g. sodium salts, of bile acids, e.g. cholanic acid, etc.

The term "sugar esters" refers to esters of sugars with fatty acids, e.g. $C_{12}$-$C_{18}$ fatty acids, e.g. fatty acids of sucrose like sucrose stearate or sucrose palmitate.

The term "poloxamer" refers to a co-polymer of polyethylenglykols and polypropylenglykols, e.g. of general formula

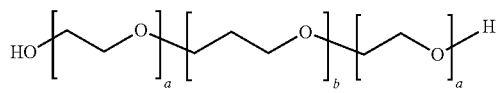

with a is 2-130, b is 15-67.

The above compounds are known in the art and commercially available.

The term "pharmaceutically acceptable" as used herein means that the buffer or salts are acceptable from a toxicity viewpoint.

Preferred surfactants may be selected from the group consisting of vitamin E polyethylene glycol 1000 succinate, e.g. TPGS, Eastman Chemicals; polyethoxylated castor oil, e.g. Cremophor El, BASF; and polyethylene glycol 40 stearate, Myri 52, Serva, Crodet S40 Croda.

The surfactants are usually present in an amount of at least 0.1% of the total weight of the composition, preferably in an amount of 0.1 to 90%, more preferably in an amount of 1 to 20%.

The presence of at least one dispersant is important for accelerating the initial dispersion of the materials in the physiological milieu where the lipase inhibitor must act. Dispersants can be chosen from water and lipid soluble compounds. They are usually present in an amount of at least 5% of the total weight of the composition, preferably in amounts varying between 5 and 70% of the total weight of the composition.

One embodiment of the present invention refers to water-soluble dispersants. Suitable water soluble dispersing agents can be found in the group consisting of sugars, sugar alcohols, alcohols, effervescents, excipients, capsule disintegrants, tablet disintegrants and mixtures thereof. More preferred dispersants may be chosen from the group consisting of glucose, sorbitol, mannitol, maltodextrin, lactose, sucrose, polyethylenglycol, glycerol, triacetin, glycofurol, effervescents, like effervescents, e.g. $NaHCO_3$/acid mixtures, e.g. $NaHCO_3$/citric acid, and mixtures thereof. Most preferred water soluble dispersants are sorbitol, mannitol, maltodextrin, lactose, sucrose, polyethylenglycol, e.g. polyethylenglycol 100-10000, more preferably polyethylenglycol 400-6000, e.g. polyethylenglycol 400, glycerol, triacetin, glycofurol and mixtures thereof. Gammascintigraphic studies have shown that effervescent mixtures ($NaHCO_3$/citric acid) have pronounced effects on the dispersion of lipidic fills of hydroxypropylmethylcellulose (HPMC) capsules in the stomach.

Compositions of the invention comprising lipid soluble compounds as dispersion agents are known as Self-Emulsifying Drug Delivery Systems (SEDDS). SEDDS have the particular characteristic of emulsifying under conditions of gentle agitation and can be termed microemulsions in case they contain water. A description of compositions of SEDDS can be found for instance in C. W. Pouton, *Advanced Drug Delivery Reviews*, 25, (1997), 47-58. It has been observed that, after dispersion in aqueous environment, compositions of a lipase inhibitor in SEDDS separate into a clear micellar phase and in lipid droplets, wherein the lipase inhibitor is present in both phases.

Accordingly, another aspect of the present invention are pharmaceutical compositions as described above comprising at least one dispersant which is a lipid soluble compound and is liquid at the body temperature.

According to the present invention the lipid soluble dispersing agent is preferably applied in amounts varying between 20 and 90% of the total weight of the compositions and must be liquid at the body temperature (i.e. >37° C.). The dispersants can be chosen among the group consisting of triglycerides, modified triglycerides, diglycerides, modified diglycerides, monoglycerides, modified monoglycerides, mixtures of modified or non-modified di/mono/triglycerides, vitamin E, tocophero acetate, terpenes, squalene and mixtures thereof, more preferably the lipid soluble compound is chosen from the group consisting of triglycerides, diglycerides, monoglycerides, modified monoglycerides, mixtures of di/mono/triglycerides, vitamin E, tocopherol acetate, and mixtures thereof. Preferred examples are medium chain triglycerides or mixtures of medium chain triglycerides, e.g. fractionated coconut oil (Medium Chain Triglycerides, MCT, e.g. Miglyol 812, Hüls AG, Neobee M-5, Stepan, Captex 355, Abitec. Preferably, the compositions according to the present invention may further comprise an additional surfactant (co-surfactant).

The term "glyceride ester" or "glyceride" refers to an ester of glycerol with fatty acids with 2 to 7 (short; short chain glycerides), 8 to 12 (medium; medium chain glycerides) and >12 (long; long chain glycerides) carbon atoms. Examples are glyceryl trilaurate, glyceryl tristearate, etc. Examples for diglycerides are glyceryl dilaurate, glyceryl distearate, ect. Examples for monoglycerides are glyceryl monolaurate and glyceryl monostearate. The invention also comprises the corresponding mixtures of mono-, di- and triglycerides. The term modified in this context refers to modified glycerides, e.g. wherein one or more fatty acids have been replaced by other fatty acids or wherein the fatty acid moieties have been chemically modified.

The compositions according to the present invention can be administered using conventional dosage forms such as hydroxypropylmethylcellulose (HPMC) capsules, soft gelatin capsules, hard gelatin capsules, starch capsules, tablets, chewable tablets and capsules, syrups, etc.

The invention is useful with any inhibitor of lipases, but is especially useful for inhibitors of the gastric and pancreatic lipase and, in particular, for the active compound orlistat. A preferred composition of the present invention comprises a) 1 to 50% lipase inhibitor of the total weight of the composition
b) 5 to 70% of at least one dispersant of the total weight of the composition
c) 0.1 to 90% of at least one surfactant of the total weight of the composition, and optionally
d) one or more pharmaceutically acceptable excipient(s).

More preferably, the lipase inhibitor, e.g. orlistat, is present in an amount of 3-30% and the surfactant in an amount of 1-20%. The present invention relates also to a process for preparing pharmaceutical compositions as described above, which process comprises mixing at least one inhibitor of lipases with at least one surfactant and at least one dispersant.

A further aspect of the present invention is to provide a method for controlling or preventing obesity comprising the step of administering to a patient a pharmaceutical composition as described above.

The invention also relates to the use a composition as defined above for the preparation of a medicament for the prevention and treatment of obesity.

The invention will be now illustrated in details by the following examples.

The efficacies on fat excretion of orlistat compositions according to examples 1-7 and of Xenical® as a reference are reported in table 1.

EXAMPLES

Example 1

150 mg of MCT (Medium Chain Triglycerides, fractionated coconut oil, Miglyol 812, Hüls AG; Neobee M-5, Stepan; Captex 355, Abitec) and 120 mg vitamin E polyethylene glycol 1000 succinate (TPGS, Eastman Chemicals) were weighed into a glass container and mixed by heating/stirring at 45° C. 30 mg orlistat were then dissolved in the so obtained clear liquid and stirred till homogeneity. 200 mg of finely milled effervescent vitamin C tablets were added under stirring and upon cooling to room temperature (25° C.), wherein the mixture solidified. The so obtained composition was filled into hydroxypropylmethylcellulose capsules.

Capsules containing 60 mg orlistat in the above composition were applied to human volunteers during a single meal test. Human subjects consumed a meal consisting of 130 g hamburger meat, 10 g butter and 100 g French fries (fried in peanut oil) and containing overall about 35 g fat. Stools were collected from day —1 (a day before eating the single meal) until day 5 after the test meal. The first and the last stools were employed to assess background fat excretion. Stools were stored frozen and extracted for total lipid according to Bligh and Dyer (Bligh, E. G., and Dyer, W. J., Can. J. Biochem. Physiol., 37, (1959), 911). Background excretion of lipids was subtracted to obtain the amount of fat excreted due to the orlistat treatment. The excreted fat was quantified by gravimetry and expressed as percentage of the fat content of the test meal.

Example 2

A composition consisting of 180 mg Cremophor EL (polyethoxylated castor oil, BASF), 60 mg MCT, 60 mg orlistat and 200 mg of finely milled effervescent vitamin C tablets was obtained according to the preparation described in example 1. Hydroxypropylmethylcellulose capsules containing each 60 mg orlistat in the above composition were applied to human volunteers according to the method described in example 1.

Example 3

A composition consisting of 450 mg Gelucire 44/14 (lauroyl macrogol-32 glycerides, Gattefossé, France), 90 mg MCT, 60 mg orlistat and 200 mg of finely milled effervescent vitamin C tablets was obtained according to the preparation described in example 1. Hydroxypropylmethylcellulose capsules containing each 60 mg of orlistat in the above composition were applied to human volunteers according to the method described in example 1.

Example 4

The composition of example 1 was prepared, except that instead of an effervescent mixture, 200 mg finely milled glucose was used as an additional excipient. Hydroxypropylmethyl-cellulose capsules containing each 30 mg of orlistat in the above composition were applied to human volunteers according to the method described in example 1.

Example 5

A composition consisting of 1700 mg TPGS and 300 mg orlistat were added to a planet-mixer in which the metal beaker was warmed to 60° C. After melting, the mixture was stirred and 10 g of solid sorbitol was added while continuously stirring at 150 rpm. The stirring was continued for 30 minutes during which time the preparation cooled down to room temperature. Afterwards, the solid mixture was sieved through a 2 mm sieve. Hydroxypropyl-methylcellulose capsules containing each 30 mg of orlistat in the above composition were applied to human volunteers according to the method described in example 1.

Example 6

210 mg polyethylene glycol 400 (PEG 400, Clariant) were mixed with 300 mg glycerol. 30 mg polyethylene glycol 40 stearate (Myrj 52, Serva Germany; Crodet S40, Croda UK) were added. The mixture was heated to 60° C. and subsequently cooled down to room temperature under stirring. 60 mg orlistat were than added to the so obtained suspension and stirred till homogeneity. The so obtained composition was filled into hydroxypropylmethylcellulose capsules. Capsules containing 60 mg orlistat in the above composition were applied to human volunteers according to the method described in example 1.

Example 7

340 mg glycerol were mixed with 30 mg polyethylene glycol 40 stearate. The mixture was heated to 60° C. and subsequently under stirring cooled down to room temperature. 30 mg orlistat, 100 mg polyethylene glycol 400 (PEG 400) and 100 glucose were then added to the so obtained solution and stirred till homogeneity. Hydroxypropylmethyl-cellulose capsules containing 30 mg orlistat in the above composition were applied to human volunteers according to the method described in example 1.

As shown in Table 1, the efficacy and/or potency of the compositions according to the present invention is much higher than that of conventional formulations. Compositions according to the invention containing just the half or even a quarter of the lipase inhibitor of the known composition are much more efficacious and/or potent. For the same lipase inhibition degree, it is now possible to strongly decrease the amount of active compound in the composition, thus minimizing undesired side effects.

Table 1 shows also the number of stool samples containing free oil for each of the above compositions. Stool samples obtained after intake of compositions according to the present invention show no or just occasional separation of oil from the main stool mass. The compositions according to the present invention enable therefore to minimize or completely suppress anal leakage of oil which is one of the most undesired side effect of the prior art compositions.

TABLE 1

In vivo results

| Example | Orlistat dose (mg) | Excreted fat (%)[1] | n[2] | Free oil in stool samples[3] |
|---|---|---|---|---|
| Reference | 120 mg (Xenical ®) | 41.8 ± 11.5 | 18 | 9/18 |
| 1 | 60 mg | 64.5 ± 3.0 | 5 | 1/5 |
| 2 | 60 mg | 72.0 ± 3.4 | 5 | 0/5 |
| 3 | 60 mg | 61.1 ± 10.0 | 4 | 0/5 |
| 4 | 30 mg | 39.9 ± 11.4 | 5 | 0/5 |
| 5 | 30 mg | 57.6 ± 27.8 | 5 | 0/5 |
| 6 | 60 mg | 53.7 ± 13.0 | 5 | 0/5 |
| 7 | 30 mg | 26.5 ± 9.9 | 5 | 0/5 |

[1]percentage of excreted fat as percentage of fat intake.
[2]number of volunteers subjected to the experiments
[3]number of stool samples containing free oil The subject invention has been described in terms of its preferred embodiments. Upon reading the present specification, various alternative embodiments will become obvious to the skilled artisan. These variations are to be considered within the scope and spirit of the subject invention, which is only to be limited by the claims that follow and their equivalents.

What is claimed is:

1. A pharmaceutical dosage form comprising (i) orlistat (ii) at least one non-ionic or zwitterionic surfactant selected from the group consisting of vitamin E polyethylene glycol 1000 succinate, polyoxyethylene sorbitan fatty acid esters, polyoxyethylene stearates, polyoxyethylene alkyl ethers, polyoxyethylene castor oils, polyglycolyzed glycerides, transesterified and (poly)ethoxylated oils, sorbitan fatty acid esters, poloxamers, lecithins, sugar esters, and mixtures thereof, and (iii) at least one dispersant.

2. The pharmaceutical dosage form according to claim 1, wherein the surfactant is selected from the group consisting of vitamin E polyethylene glycol 1000 succinate, polyethoxylated castor oil, and polyethylene glycol 40 stearate.

3. The pharmaceutical dosage form according to claim 1, wherein the surfactant is present in an amount of at least 0.1% of the total weight of the composition.

4. The pharmaceutical dosage form according to claim 3, wherein the surfactant is present in an amount of 0.1% to 90% of the total weight of the composition.

5. The pharmaceutical dosage form according to claim 1, wherein the dispersant is a water-soluble dispersant.

6. The pharmaceutical dosage form according to claim 5, wherein the dispersant is selected from the group consisting of sugars, sugar alcohols, alcohols, effervescents, excipients, capsule disintegrants, tablet disintegrants, and mixtures thereof.

7. The pharmaceutical dosage form according to claim 6, wherein the dispersant is chosen from the group consisting of glucose, sorbitol, mannito,-maltodextrin, lactose, sucrose, polyethylenglycol, glycerol, triacetin, glycofurol, effervescents, and mixtures thereof.

8. The pharmaceutical dosage form according to claim 7, wherein the dispersant is chosen from the group consisting of sorbitol, mannitol, maltodextrin, lactose, sucrose, polyethylenglycol, glycerol, triacetin, glycofurol, and mixtures thereof.

9. The pharmaceutical dosage form according to claim 1, wherein the dispersant is a lipid-soluble compound that is liquid at human body temperature.

10. The pharmaceutical dosage form according to claim 9, wherein the lipid-soluble compound is chosen from the group consisting of triglycerides, modified triglycerides, diglycerides, modified diglycerides, monoglycerides, modified monoglycerides, mixtures of modified or non-modified di/mono/triglycerides, vitamin E, tocopherol acetate, terpenes, squalene, and mixtures thereof.

11. The pharmaceutical dosage form according to claim 10, wherein the lipid-soluble compound is chosen from the group consisting of triglycerides, diglycerides, monoglycerides, mixtures of mono/di/triglycerides, vitamin E, tocopherol acetate, and mixtures thereof.

12. The pharmaceutical dosage form according to claim 11, wherein the lipid-soluble compound is a medium chain triglyceride or a mixture of medium chain triglycerides.

13. The pharmaceutical dosage form according to claim 1, wherein the dispersant is present in an amount of at least 5% of the total weight of the composition.

14. The pharmaceutical dosage form according to claim 13, wherein the dispersant is present in amounts varying between 5% and 70% of the total weight of the composition.

15. The pharmaceutical dosage form according to claim 1, wherein the dispersant is a lipid-soluble compound present in an amount varying between 20 and 90% of the total weight of the composition.

16. The pharmaceutical dosage form according to claim 1, which comprises at least two surfactants.

17. The pharmaceutical dosage form according to claim 1, wherein orlistat is present in an amount from 5% to 30% of the total weight of the composition.

18. The pharmaceutical dosage form according to claim 1 further comprising pharmaceutically acceptable excipients selected from the group consisting of carbohydrates, antioxidants, co-solvents, thickening agents, preservatives, and lubricants.

19. The pharmaceutical dosage form according to claim 1, which comprises a) 1% to 30% orlistat of the total weight of the composition b) 5% to 70% of at least one dispersant of the total weight of the composition and c) 0.1% to 90% of at least one surfactant of the total weight of the composition.

20. The pharmaceutical dosage form according to claim 19 further comprising one or more pharmaceutically acceptable excipients.

21. The pharmaceutical dosage form according to claim 1 wherein the at least one surfactant is a polyoxyethylene stearate.

22. The pharmaceutical dosage form according to claim 6 wherein the at least one surfactant is a polyoxyethylene stearate.

23. A method for improving the efficacy of orlistat in a mammal in need thereof comprising administering to said mammal a pharmaceutical dosage form comprising (i) orlistat present in an amount of 60 mg or less (ii) at least one non-ionic or zwitterionic surfactant selected from the group consisting of vitamin E polyethylene glycol 1000 succinate, polyoxyethylene sorbitan fatty acid esters, polyoxyethylene stearates, polyoxyethylene alkyl ethers, polyoxyethylene castor oils, polyglycolyzed glycerides, transesterified and (poly) ethoxylated oils, sorbitan fatty acid esters, poloxamers, lecithins, sugar esters, and mixtures thereof, and (iii) at least one dispersant.

* * * * *

UNITED STATES PATENT AND TRADEMARK OFFICE
CERTIFICATE OF CORRECTION

| | | |
|---|---|---|
| PATENT NO. | : 8,012,494 B2 | Page 1 of 1 |
| APPLICATION NO. | : 10/794123 | |
| DATED | : September 6, 2011 | |
| INVENTOR(S) | : Passchier Christiaan de Smidt et al. | |

It is certified that error appears in the above-identified patent and that said Letters Patent is hereby corrected as shown below:

In column 1, page 1, Related U.S. Application Data, second line, delete "and" and insert --which is--.

Signed and Sealed this
Eighteenth Day of October, 2011

David J. Kappos
*Director of the United States Patent and Trademark Office*